(12) United States Patent
Mehl

(10) Patent No.: US 12,318,087 B2
(45) Date of Patent: Jun. 3, 2025

(54) VERTEBRAL DISC AUGER

(71) Applicant: Life Spine, Inc., Huntley, IL (US)

(72) Inventor: David T. Mehl, Lake in the Hills, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 18/785,405

(22) Filed: Jul. 26, 2024

(65) Prior Publication Data

US 2024/0382195 A1 Nov. 21, 2024

Related U.S. Application Data

(63) Continuation of application No. 18/113,819, filed on Feb. 24, 2023, now abandoned.

(51) Int. Cl.
| | |
|---|---|
| *A61B 17/068* | (2006.01) |
| *A61B 17/02* | (2006.01) |
| *A61B 17/064* | (2006.01) |
| *A61B 17/072* | (2006.01) |

(Continued)

(52) U.S. Cl.
CPC .......... *A61B 17/068* (2013.01); *A61B 17/025* (2013.01); *A61B 17/064* (2013.01); *A61B 17/072* (2013.01); *A61B 17/32002* (2013.01); *A61B 17/1615* (2013.01); *A61B 17/1617* (2013.01); *A61B 17/320016* (2013.01)

(58) Field of Classification Search
CPC ... A61B 17/064; A61B 17/068; A61B 17/072; A61B 17/02; A61B 17/025; A61B 17/16; A61B 17/164; A61B 17/1615; A61B 17/1617; A61B 17/1631; A61B 17/1635; A61B 17/1671; A61B 17/1757; A61B 17/8833; A61B 17/32002; A61B 17/320016
USPC ......... 227/19, 175.1; 606/1, 79, 90, 92, 139, 606/180, 219
See application file for complete search history.

(56) References Cited

U.S. PATENT DOCUMENTS

| | | | | |
|---|---|---|---|---|
| 4,646,738 | A | * | 3/1987 | Trott ................ A61B 17/32002 604/266 |
| 5,366,468 | A | * | 11/1994 | Fucci ............... A61B 17/32002 606/180 |
| 5,759,185 | A | | 6/1998 | Grinberg |

(Continued)

FOREIGN PATENT DOCUMENTS

| | | |
|---|---|---|
| DE | 202011002653 U1 | 6/2011 |
| WO | 2007104837 A1 | 9/2007 |

*Primary Examiner* — Scott A Smith
(74) *Attorney, Agent, or Firm* — Bruce J. Bowman

(57) ABSTRACT

A medical instrument for shaving, collecting, and removing vertebral disc material from a vertebral disc space of a spine, has a shaft defining a proximal shaft end and a distal shaft end, and an auger at the distal shaft end. The auger has a plurality of helical cutting flutes configured to shave and collect vertebral disc material from the vertebral disc through rotation of the auger. Each helical cutting flute has a cutting apex that together define a cutting tip, and a radially inward helical slot that collectively define an internal cavity for collection of cut vertebral disc material. The plurality of cutting apexes converge at the cutting tip, defining a point. The medical instrument includes a connector to allow attachment of a handle. A notch in the proximal shaft end that receives a flange of the handle prevents rotation of the handle relative to the auger.

10 Claims, 3 Drawing Sheets

(51) Int. Cl.
*A61B 17/32* (2006.01)
*A61B 17/16* (2006.01)

(56) References Cited

U.S. PATENT DOCUMENTS

| | | | |
|---|---|---|---|
| 5,851,208 A | 12/1998 | Trott | |
| 5,857,995 A | 1/1999 | Thomas et al. | |
| 5,913,867 A * | 6/1999 | Dion | A61B 17/32002 606/180 |
| 6,648,895 B2 * | 11/2003 | Burkus | A61B 17/025 606/90 |
| 6,743,234 B2 * | 6/2004 | Burkus | A61B 17/025 606/90 |
| 6,783,533 B2 * | 8/2004 | Green | A61B 17/164 606/80 |
| 7,169,183 B2 * | 1/2007 | Liu | A61F 2/447 623/17.16 |
| 7,226,459 B2 * | 6/2007 | Cesarini | A61B 17/32002 |
| 7,572,263 B2 * | 8/2009 | Preissman | A61B 17/8833 606/92 |
| 8,486,074 B2 * | 7/2013 | Steiner | A61B 17/1635 606/79 |
| 9,622,756 B2 * | 4/2017 | Loreth | A61B 17/1631 |
| 9,636,131 B2 * | 5/2017 | Manley | A61B 17/1615 |
| 9,974,548 B2 * | 5/2018 | Russo | A61B 17/1615 |
| 10,022,245 B2 * | 7/2018 | Frasier | A61F 2/442 |
| 10,470,786 B2 * | 11/2019 | Deeny | A61B 17/32002 |
| 10,772,652 B2 * | 9/2020 | Shener-Irmakoglu | A61B 1/018 |
| 10,898,218 B2 * | 1/2021 | Prokop | A61B 17/320016 |
| 11,045,287 B2 * | 6/2021 | Burke | A61B 17/1673 |
| 11,376,032 B2 * | 7/2022 | Wood | A61B 17/32002 |
| 2005/0283160 A1 * | 12/2005 | Knisely | A61B 17/16 606/80 |
| 2006/0217728 A1 * | 9/2006 | Chervitz | A61B 17/1757 606/79 |
| 2008/0132929 A1 * | 6/2008 | O'Sullivan | A61B 17/1615 606/170 |
| 2018/0228499 A1 | 8/2018 | Wecker et al. | |
| 2020/0352579 A1 | 11/2020 | Davis et al. | |

\* cited by examiner

VERTEBRAL DISC AUGER

CROSS-REFERENCE TO RELATED APPLICATIONS

This U.S. non-provisional patent application is a continuation of U.S. non-provisional patent application Ser. No. 18/113,819 filed Feb. 24, 2023 titled "Vertebral Disc Auger" which claims the benefit of and/or priority under 35 U.S.C. § 119(e) to U.S. provisional patent application Ser. No. 63/314,017 filed Feb. 25, 2022 titled "Vertebral Disc Auger," the entire contents of each of which is specifically incorporated herein by reference.

FIELD OF THE INVENTION

The present invention relates to instruments for spine procedures and, more particularly, to instruments for removing vertebral disc material from a vertebral disc space of a spine.

BACKGROUND OF THE INVENTION

A large majority of people develop spine issues because of age, disease, trauma, acquired complication, and/or other reason. Some spine issues can be alleviated without surgery while other spine issues necessitate surgery. In some circumstances, it may be necessary to remove vertebral disc material from between adjacent vertebrae of the spine. Such a procedure is now routinely accomplished using minimally invasive surgery or micro invasive surgery (collectively, MIS). Both procedures reduce bodily trauma by utilizing surgical instruments that are introduced into the body via a small incision via a cannula and/or an endoscope (i.e. tube). The medical instrument is inserted into and through the tube and operated accordingly.

Various forms of medical instruments are known to provide vertebral disc material collection and/or removal. Many, however, are not suitable for use in MIS. One form of suitable MIS medical instrument for removing vertebral disc material from the vertebral disc space of adjacent vertebrae of the spine is an auger. A vertebral disc material auger for MIS has a head designed for insertion into and through a tube for harvesting vertebral disc tissue. Current MIS augers for harvesting vertebral disc material from a vertebral disc space between adjacent vertebrae of a spine however, are deficient in various respects.

It would therefore be advantageous to have an MIS medical instrument for harvesting vertebral disc material that overcomes the deficiencies of the prior art. It would therefore be further advantageous to have an MIS auger for harvesting vertebral disc material that reduces surgical complexity. It would furthermore be advantageous to have an auger for an MIS spine procedure that provides efficient collecting and removing of vertebral disc material.

The present MIS medical instrument addresses the above and more.

SUMMARY OF THE INVENTION

A medical instrument for removing vertebral disc material particularly, but not necessarily, during an MIS spine procedure, has a proximal end configured as or for attachment to a handle, a shaft extending from the proximal end, and a head formed as an auger at a distal end of the shaft, the auger having a plurality of cutting flutes configured to shave and collect vertebral disc material from a vertebral disc in a vertebral disc space of a spine through rotation of the auger.

The cutting flutes spiral or twist along a longitudinal axis of the shaft. In one form, the auger has three spiral cutting flutes, each spiral cutting flute making a 120° rotation about the head along the longitudinal axis of the shaft from a tip. Other numbers of spiral cutting flutes as well as their amount of rotation about the head along the longitudinal axis of the shaft are contemplated and may be used. Each one of the plurality of spiral cutting flutes extends from an angled apex which together, form the tip at the distal end of the auger.

A cavity is formed in the auger with each one of the plurality of spiral cutting flutes having a radially inward slot in communication with the cavity. Each slot extends along the longitudinal axis of the respective spiral cutting flute. The internal cavity of the auger and the slots of the spiral cutting flutes together define an area for collection of cut vertebral disc material.

The proximal end may include a notch or other structure configured to receive a flange or other structure of a handle, or configured as a handle.

The auger may extend from a neck at the distal end of the shaft with each one of the plurality of spiral cutting flutes having a proximal end that extends from the neck, each one of the proximal ends of the spiral cutting flutes having a surface sloped radially inward from the neck.

Further aspects of the present invention will become apparent from consideration of the drawings and the following description of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention and its features will be better understood by reference to the accompanying drawings, wherein.

Figure 1:
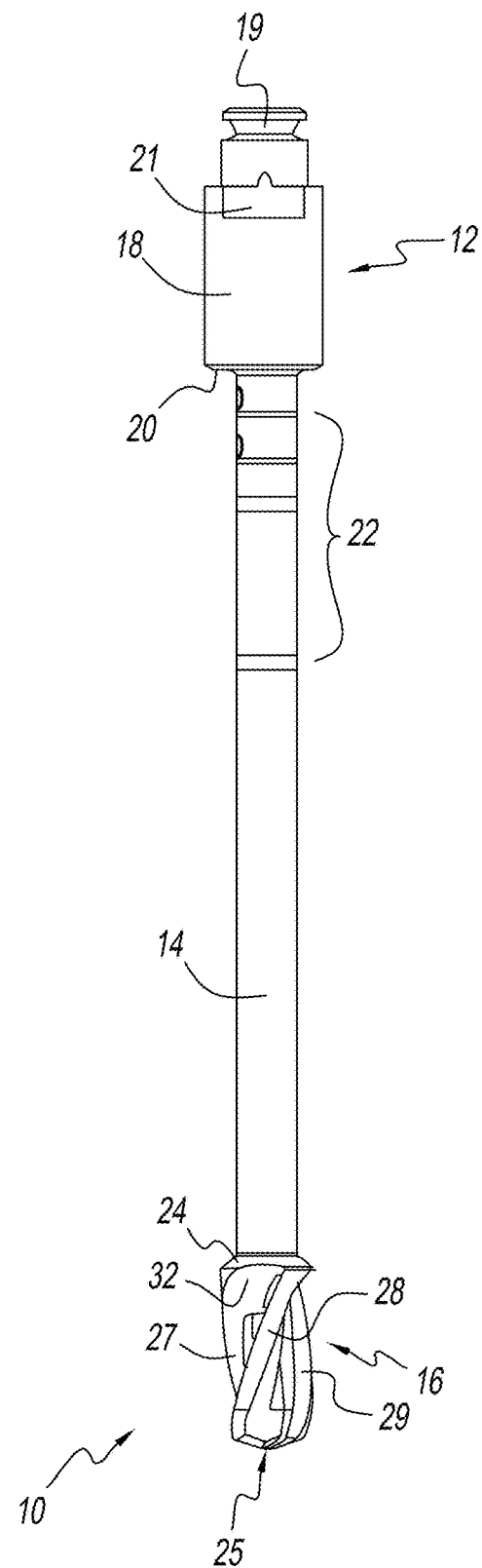
FIG. 1 is a side view of a medical instrument for removing vertebral disc material from a vertebral disc space of a spine fashioned in accordance with the present principles.

For the purposes of promoting an understanding of the principles of the invention reference will now be made to the embodiment illustrated in the drawings and specific language will be used to describe the same. It will nevertheless be understood that no limitation of the scope of the invention is thereby intended. Any alterations and further modifications in the described embodiment, and any further applications of the principles of the invention as described herein are contemplated as would normally occur to one skilled in the art to which the invention relates.

DETAILED DESCRIPTION OF THE INVENTION

Referring to FIGS. 1-5, there is shown a medical instrument, generally designated 10, for removing vertebral disc material (not shown), typically from within a disc space (not shown) between adjacent vertebrae (not shown) of a spine during a surgical spine procedure, particularly, but not necessarily, in minimally invasive or micro invasive surgery (MIS) via a cannula, endoscopic, tube, or the like, or a similar spine procedure. The present medical instrument 10 may be used in surgical procedures other than MIS procedures. The medical instrument 10 is fashioned from one or more surgical grade materials.

FIG. 1 depicts an overall view of the medical instrument 10, also termed a vertebral disc auger. The vertebral disc auger 10 has a proximal end 12 configured as to define a handle or handle receptor (collectively, handle 12), a shaft 14 connected to a distal end 20 of the handle 12, and a head 16 fashioned as an auger connected to a distal end of the shaft 14 through a neck 24. The handle 12 is characterized by a cylindrical body 18 sized to accommodate a hand (not shown) or a handle via a generally conical connector 19 at a proximal end of the cylindrical body 18, and to the distal end 20. The connector 19 is configured to allow connection to a handle (not seen). Alternately, a handle (not seen) may be attached to the connector 19 as a permanent part of the vertebral disc auger 10, or the configuration as shown can be the handle. The cylindrical body 18 is shown with a notch 21 that is configured to receive a handle. The cylindrical body 18 may have additional notches (not shown) or other configuration(s) that would be designed to receive a handle. The notch 21 (and any additional notches/configuration(s)) provide anti-rotation of a handle with respect to the cylindrical body 18 such that rotation of the handle will rotate the shaft 14 and auger 16. The distal end 20 of the cylindrical body 18 is generally planar and can serve as a stop against further insertion into an MIS tube, endoscope, cannula, or the like (not shown, and collectively "cannula") during use. Rotation of the cylindrical body 18 rotates the shaft 14 and thus the auger 16.

Figure 2:
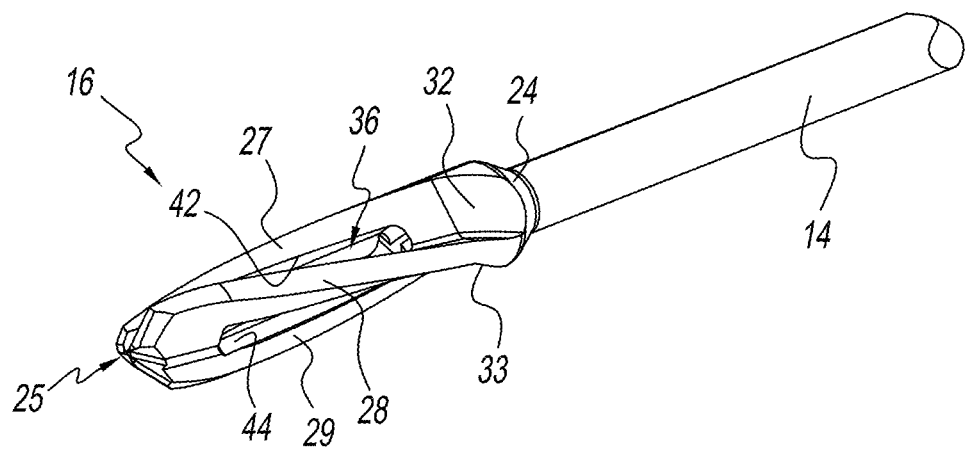
FIG. 2 is an enlarged view of a distal end of the medical instrument of FIG. 1 particularly depicting a head thereof in the form of an auger.
Figure 3:
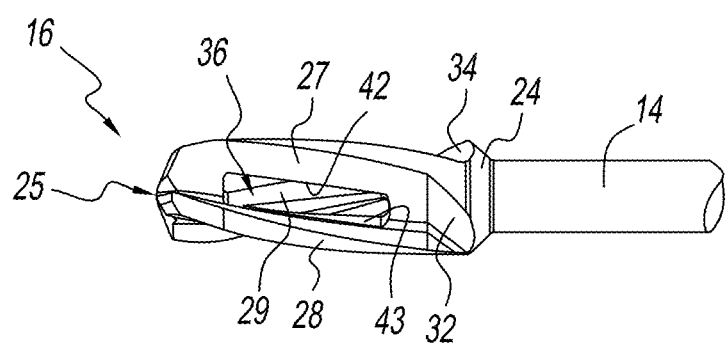
FIG. 3 is an enlarged view of the auger of the medical instrument of FIG. 1.
Figure 4:
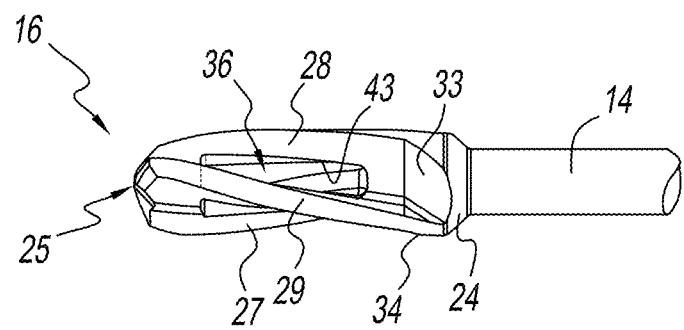
FIG. 4 is another enlarged view of the auger of the medical instrument of FIG. 1 rotated 90° with respect to the view of FIG. 4.

FIGS. 2-4 depict various views of the auger 16. The auger 16 is configured to cut, shave, or otherwise remove vertebral discs/disc material (not shown) from a spine (not shown), collect the shaven vertebral disc material, and remove the collected vertebral disc material. Cutting and collecting the vertebral disc material is accomplished by rotation of the auger 16. Removal of the vertebral disc material is accomplished by removing the auger 16 from the vertebral disc space and from the cannula.

The auger 16 has a plurality of helical cutting flutes or blades for slicing into vertebral disc material. In the embodiment shown in the figures, the auger 16 has three (3) helical cutting flutes 27, 28, 29. Each helical cutting flute 27, 28, 29 extends from a respective sloped surface 32, 33, 34 at a distal end of the neck 24, winds or spirals around the auger 16, relative to a longitudinal axis of the shaft 14, and terminates in a cutting tip 25. Each flute spirals or twists 120° from its apex (sloped surfaces) along the longitudinal axis of the shaft 14. Other numbers of cutting flutes may be provided as well as the amount of twist along the longitudinal axis of the shaft 14. Upon rotation of the auger 16, the helicity of the cutting flutes aid in advancing the auger into the disc material by creating a pathway. Each helical cutting flute 27, 28, 29 has a respective helical slot 42, 43, 44 that is situated radially inward of an outer diameter of the auger 16. The helical slots 42, 43, 44 form, or at least partially form, an internal central cavity 36 within the auger 16. The central cavity 36 collects cut/shaven disc material for removal. Removal is accomplished by extracting the auger 16 from the vertebral disc space and the body.

Figure 5:
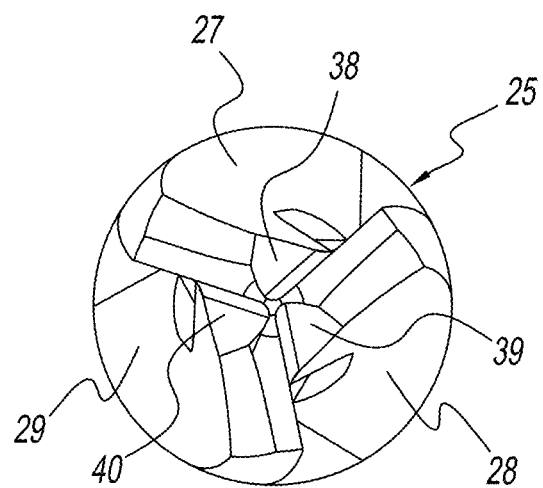
FIG. 5 is an enlarged view of a tip of the auger of the medical instrument of FIG. 1.

FIG. 5 depicts an enlarged view of the cutting tip 25 as viewed from the distal end of the auger 16. The helical cutting flute 27 terminates at its distal end in a cutting apex 38. The helical cutting flute 28 terminates at its distal end in a cutting apex 39. The helical cutting flute 29 terminates at its distal end in a cutting apex 40. The cutting apexes 38, 39, 40 converge to form the cutting tip 25.

In use, as the auger 16 advances forward into the disc material through rotation of the proximal end 12/shaft 14, the helical cutting flutes 27, 28, 29 collect disc material into the helical slots 42, 43, 44/central cavity 36 for the purpose of removing the disc material.

The shaft 14 is shown with depth markings 22 on its outside diameter for assisting with depth reference within a patient. Other types of depth markings/references may be used.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention.

What is claimed is:

1. A medical instrument for removing vertebral disc material from a vertebral disc in a vertebral disc space of a spine during a surgical spine procedure, the medical instrument comprising:
   a shaft having a proximal shaft end, a distal shaft end, and a first diameter;
   a handle receptor at the proximal shaft end and having a second diameter that is greater than the first diameter of the shaft, the handle receptor configured for reception of a handle; and
   an auger at the distal shaft end, the auger extending from a radially outward tapered neck at the distal shaft end that terminates at a third diameter that is greater than the first diameter of the shaft, the auger having three helical cutting flutes configured to shave and collect vertebral disc material from a vertebral disc in a vertebral disc space of a spine through rotation of the shaft, each one of the three helical cutting flutes having a cutting apex that all together define a cutting tip, each one of the three helical cutting flutes extending from the third diameter of the shaft to the cutting tip in a 120° rotation, with each one of the three helical cutting flutes having a radially inward helical slot that collectively define an internal cavity in the auger for collection of cut vertebral disc material.

2. The medical instrument of claim 1, wherein the three cutting apexes converge at the cutting tip to define a point.

3. The medical instrument of claim 1, wherein:
   the handle receptor comprises a cylindrical body defining a proximal cylindrical body end and a distal cylindrical body end with the distal cylindrical body end connected to the proximal shaft end; and
   the proximal cylindrical body end has a conical connector configured for reception of a handle on the handle receptor.

4. The medical instrument of claim 3, wherein the proximal cylindrical body end has a notch that receives a flange of the handle that prevents rotation of the handle relative to the cylindrical body.

5. The medical instrument of claim 4, wherein the proximal shaft end has depth markings for determining auger depth.

6. The medical instrument of claim 1, wherein the auger extends from the neck at the distal shaft end with each one of the three helical cutting flutes having a proximal end that extends from the neck, each one of the proximal ends of the helical cutting flutes having a surface sloped radially inward from the neck.

7. A medical instrument for removing vertebral disc material from a vertebral disc in a vertebral disc space of a spine, the medical instrument comprising:
   a shaft having a proximal shaft end, a distal shaft end, and a first diameter extending from the proximal shaft end to the distal shaft end;
   a handle receptor at the proximal shaft end having a second diameter that is greater than the first diameter, the handle receptor configured for reception of a handle; and
   a vertebral disc material reaming and collection head at the distal shaft end, the reaming and collection head extending from a radially outward tapered neck at the distal shaft end that terminates at a third diameter that is greater than the first diameter of the shaft, the reaming and collection head having three helical cutting flutes configured to shave and collect vertebral disc material from a vertebral disc in a vertebral disc space of a spine through rotation of the shaft, each one of the three helical cutting flutes having a cutting apex that all together define a cutting tip, each one of the three helical cutting flutes extending from the third diameter of the shaft to the cutting tip in a 120° rotation, with each one of the three helical cutting flutes having a radially inward helical slot that collectively define an internal cavity in the reaming and collection head for collection of reamed vertebral disc material.

8. The medical instrument of claim 7, wherein the reaming and collection head extends from the neck at the distal shaft end with each one of the three helical cutting flutes having a proximal end that extends from the neck, each one of the proximal ends of the helical cutting flutes having a surface sloped radially inward from the neck.

9. The medical instrument of claim 8, wherein:
   the handle receptor comprises a cylindrical body defining a proximal cylindrical body end and a distal cylindrical body end with the distal cylindrical body end connected to the proximal shaft end;
   the proximal cylindrical body end has a conical connector configured for reception of a handle on the handle receptor; and
   wherein the proximal cylindrical body end has a notch that receives a flange of the handle that prevents rotation of the handle relative to the cylindrical body.

10. The medical instrument of claim 9, wherein the proximal shaft end has depth markings for determining depth of the reaming and collection head.

* * * * *